(12) United States Patent
Perszyk et al.

(10) Patent No.: US 10,856,982 B2
(45) Date of Patent: Dec. 8, 2020

(54) TRANSAPICAL MITRAL VALVE DELIVERY SYSTEM

(71) Applicant: St. Jude Medical, Cardiology Division, Inc., St. Paul, MN (US)

(72) Inventors: Brian Joseph Perszyk, Shoreview, MN (US); Philip Osterbauer, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 184 days.

(21) Appl. No.: 16/134,354

(22) Filed: Sep. 18, 2018

(65) Prior Publication Data

US 2019/0083261 A1 Mar. 21, 2019

Related U.S. Application Data

(60) Provisional application No. 62/560,368, filed on Sep. 19, 2017.

(51) Int. Cl.
*A61F 2/24* (2006.01)
*A61F 2/962* (2013.01)
(Continued)

(52) U.S. Cl.
CPC ............ *A61F 2/2436* (2013.01); *A61F 2/243* (2013.01); *A61F 2/9517* (2020.05); *A61F 2/962* (2013.01);
(Continued)

(58) Field of Classification Search
CPC ...... A61F 2/2436; A61F 2/243; A61F 2/9517; A61F 2/966; A61F 2002/9534; A61F 2/97; A61F 2/962
See application file for complete search history.

(56) References Cited

U.S. PATENT DOCUMENTS

| 5,891,193 A | 4/1999 | Robinson et al. |
| 6,132,458 A | 10/2000 | Staehle et al. |
| (Continued) | | |

FOREIGN PATENT DOCUMENTS

| EP | 0657147 A2 | 6/1995 |
| WO | 2010042950 A2 | 4/2010 |
| (Continued) | | |

OTHER PUBLICATIONS

European Search Report for EP Application No. 18195359.7, dated Jan. 22, 2019.

(Continued)

*Primary Examiner* — Julian W Woo
(74) *Attorney, Agent, or Firm* — Lerner, David, Littenberg, Krumholz & Mentlik, LLP

(57) ABSTRACT

A delivery device for a prosthetic heart valve includes a catheter assembly and an operating handle. The catheter assembly may include an inner shaft around which a compartment for the heart valve is defined, and a distal sheath having proximal and distal segments configured to enclose the compartment. The handle may include a first lead screw coupled to the proximal segment and a second lead screw coupled to the distal segment. Actuation of the first lead screw operates to move the proximal segment of the distal sheath proximally and actuation of the second lead screw operates to move the distal segment of the distal sheath distally to uncover the compartment and deploy the heart valve.

19 Claims, 11 Drawing Sheets

(51) Int. Cl.
    *A61F 2/966*     (2013.01)
    *A61F 2/95*     (2013.01)
    *A61F 2/97*     (2013.01)

(52) U.S. Cl.
    CPC ............ *A61F 2/966* (2013.01); *A61F 2/97* (2013.01); *A61F 2002/9534* (2013.01)

(56) References Cited

U.S. PATENT DOCUMENTS

| | | | |
|---|---|---|---|
| 6,395,017 | B1 | 5/2002 | Dwyer et al. |
| 8,475,523 | B2 * | 7/2013 | Duffy .............. A61F 2/966 623/2.11 |
| 8,814,931 | B2 * | 8/2014 | Wang .............. A61F 2/2436 623/2.11 |
| 9,192,469 | B2 | 11/2015 | Mearns et al. |
| 10,517,722 | B2 * | 12/2019 | Passman .......... A61F 2/2433 |
| 10,631,984 | B2 * | 4/2020 | Nyuli .............. A61F 2/2418 |
| 2002/0120323 | A1 | 8/2002 | Thompson et al. |
| 2003/0191516 | A1 | 10/2003 | Weldon et al. |
| 2004/0127912 | A1 | 7/2004 | Rabkin et al. |
| 2005/0137692 | A1 | 6/2005 | Haug et al. |
| 2005/0182486 | A1 | 8/2005 | Gabbay |
| 2006/0259135 | A1 | 11/2006 | Navia et al. |
| 2006/0282150 | A1 | 12/2006 | Olson et al. |
| 2006/0287718 | A1 | 12/2006 | Bicer |
| 2007/0162107 | A1 | 7/2007 | Haug et al. |
| 2007/0239271 | A1 | 10/2007 | Nguyen |
| 2008/0071363 | A1 | 3/2008 | Tuval et al. |
| 2009/0054976 | A1 | 2/2009 | Tuval et al. |
| 2009/0099530 | A1 | 4/2009 | Adams et al. |
| 2010/0057185 | A1 | 3/2010 | Melsheimer et al. |
| 2010/0121434 | A1 | 5/2010 | Paul et al. |
| 2010/0262231 | A1 | 10/2010 | Tuval et al. |
| 2010/0312333 | A1 | 12/2010 | Navia et al. |
| 2011/0295216 | A1 | 12/2011 | Miller |
| 2013/0023868 | A1 | 1/2013 | Worrell et al. |
| 2013/0274870 | A1 | 10/2013 | Lombardi et al. |
| 2013/0297011 | A1 | 11/2013 | Morris et al. |
| 2014/0046428 | A1 | 2/2014 | Cragg et al. |
| 2014/0371844 | A1 | 12/2014 | Dale et al. |
| 2015/0230955 | A1 | 8/2015 | Farag Eells et al. |
| 2017/0165064 | A1 | 6/2017 | Nyuli et al. |

FOREIGN PATENT DOCUMENTS

| | | |
|---|---|---|
| WO | 2011150399 A1 | 12/2011 |
| WO | 2012127309 A1 | 9/2012 |
| WO | 2012178115 A2 | 12/2012 |
| WO | 2013028387 A2 | 2/2013 |
| WO | 2013059747 A1 | 4/2013 |

OTHER PUBLICATIONS

International Search Report and Written Opinion for Application No. PCT/US2014/042914 dated Nov. 14, 2014.

International Search Report for Application No. PCT/US2016/022748 dated Aug. 8, 2016.

Partial International Search Report for Application No. PCT/US2014/042914 dated Oct. 21, 2014.

International Search Report for Application No. PCT/US2017/032071 dated Jul. 5, 2017, 4 pages.

\* cited by examiner

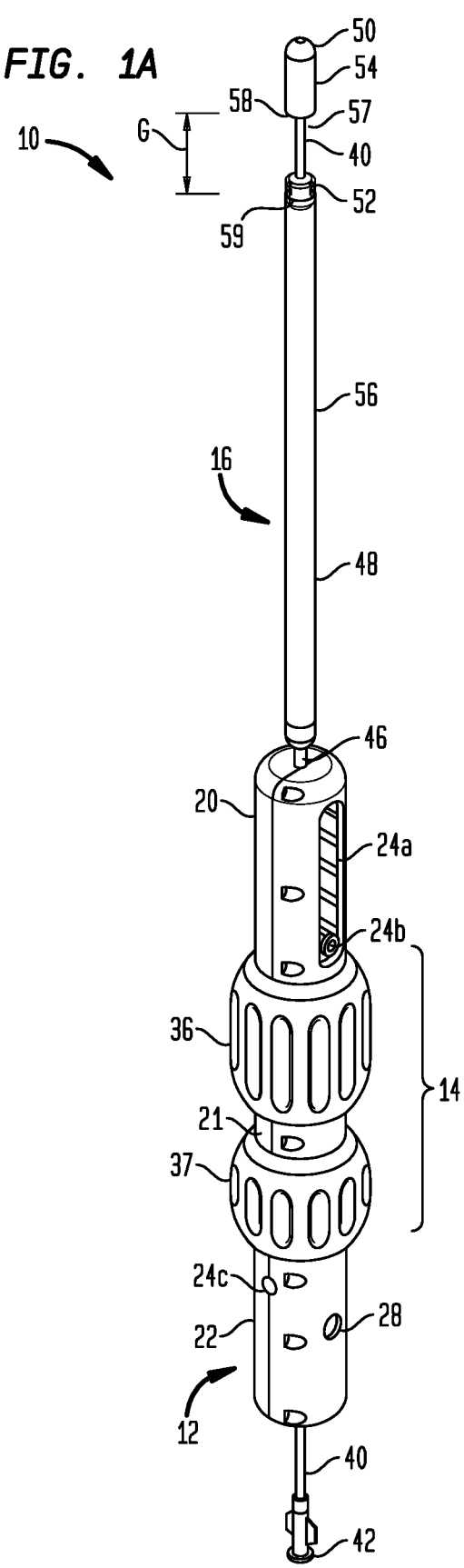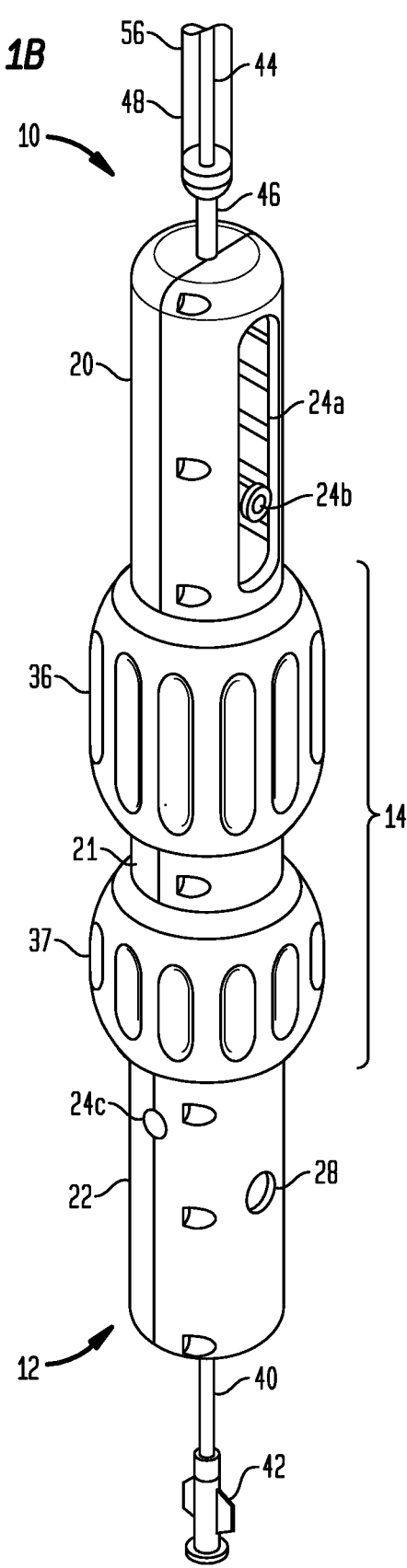

TRANSAPICAL MITRAL VALVE DELIVERY SYSTEM

CROSS-REFERENCE TO RELATED APPLICATIONS

This application claims the benefit of the filing date of U.S. Provisional Patent Application No. 62/560,368, filed on Sep. 19, 2017, the disclosure of which is hereby incorporated herein by reference.

BACKGROUND OF THE INVENTION

The present disclosure relates to heart valve replacement and, in particular, to the delivery of collapsible prosthetic heart valves into a patient for implantation. More particularly, the present disclosure relates to devices and methods for delivering and deploying collapsible prosthetic heart valves within native valve annuluses.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY OF THE INVENTION

Described herein is a delivery device for a collapsible prosthetic heart valve. The delivery device may include a catheter assembly and an operating handle coupled to the catheter assembly. The catheter assembly may include an inner shaft around which a compartment is defined, and a distal sheath having a proximal segment and a distal segment together configured to enclose the compartment. The operating handle may include a housing defining a movement space therein, the movement space extending in an elongation direction, a first elongated element fixedly coupled to the proximal segment of the distal sheath and moveable in first and second opposite longitudinal directions within the movement space, a second elongated element coupled to the distal segment of the distal sheath and moveable in the first and second longitudinal directions within the movement space, a first actuator coupled to the housing and moveable relative to the housing, the first actuator being operatively engaged with the first elongated element, and a second actuator coupled to the housing and moveable relative to the housing and relative to the first actuator, the second actuator being operatively engaged with the second elongated element. At least a portion of the first and second elongated elements may overlap in the elongation direction. Each of the first and second elongated elements may be independently longitudinally slidable relative to the other of the first and second elongated elements.

Also described herein is an operating handle for a delivery device for a collapsible prosthetic heart valve. The operating handle may include a housing defining a movement space therein, the movement space extending in an elongation direction, a first elongated element moveable in first and second opposite longitudinal directions within the movement space, a second elongated element moveable in the first and second longitudinal directions within the movement space, a first actuator coupled to the housing and moveable relative to the housing, the first actuator being operatively engaged with the first elongated element, and second actuator coupled to the housing and moveable relative to the housing and relative to the first actuator, the second actuator being operatively engaged with the second elongated element. At least a portion of the first and second elongated elements may overlap in the elongation direction. Each of the first and second elongated elements may be independently longitudinally slidable relative to the other of the first and second elongated elements.

Further described herein is a method of delivering a collapsible prosthetic heart valve in a patient. The method may include providing a delivery device having a catheter assembly and an operating handle. The catheter assembly may include a compartment adapted to receive the valve in an assembled condition and a distal sheath slidable relative to the compartment. The distal sheath may have a proximal segment and a distal segment. The operating handle may include housing defining a movement space therein and first and second elongated elements each independently moveable in first and second opposite longitudinal directions within the movement space. The method may also include loading the valve into the compartment of the catheter assembly and covering the compartment and the valve with the proximal and distal segments of the distal sheath, and inserting the catheter assembly into the patient so that the valve is positioned at a target location within the patient.

The method may further include partially deploying a first end of the valve by moving the first elongated element in the first longitudinal direction within the movement space, whereby the proximal segment of the distal sheath is moved a first distance in the first longitudinal direction. The method may also include deploying a second end of the valve by moving the second elongated element in the second longitudinal direction within the movement space, whereby the distal segment of the distal sheath is moved in the second longitudinal direction. The method may further include fully deploying the first end of the valve by continuing movement of the first elongated element in the first longitudinal direction within the movement space, whereby the proximal segment of the distal sheath is moved a further distance in the first longitudinal direction.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

FIG. 1A is a perspective view of a delivery device with a proximal segment of a distal sheath being shown in a fully-retracted position;

FIG. 1B is a perspective view of the delivery device of FIG. 1A with the proximal segment of the distal sheath being shown as partially transparent;

DETAILED DESCRIPTION

There is a need for further improvements to the devices, systems, and methods for transcatheter delivery and deployment of collapsible prosthetic heart valves, and in particular, self-expanding prosthetic heart valves. Among other advantages, the present invention may address one or more of these needs.

Figure 3A:
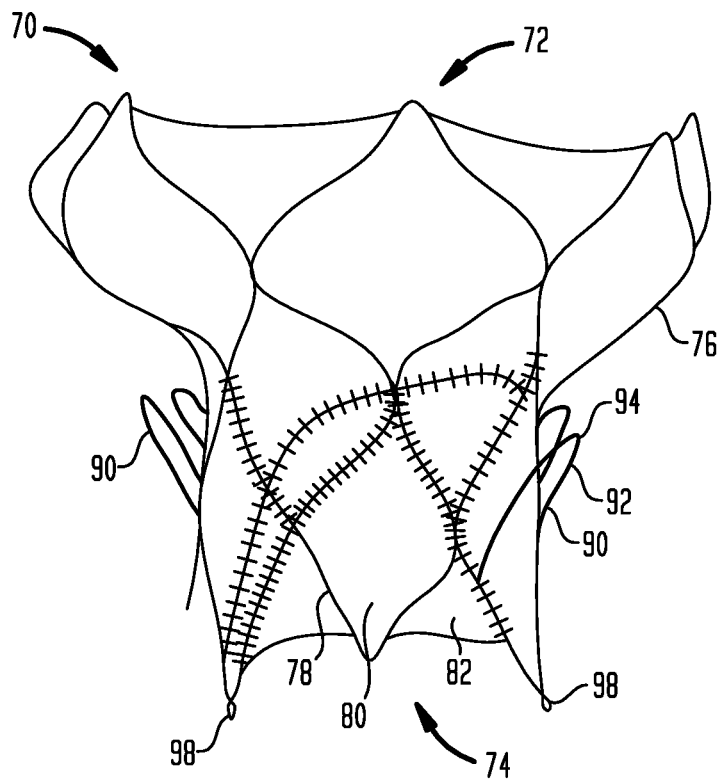
FIG. 3A is a side view of a self-expanding prosthetic heart valve suitable for deployment with the delivery device of FIG. 1A.
Figure 3B:
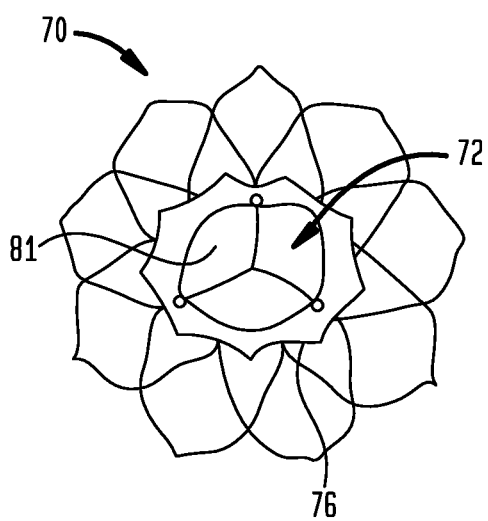
FIG. 3B is a view of the prosthetic heart valve of FIG. 3A from the inlet end.
Figure 3C:
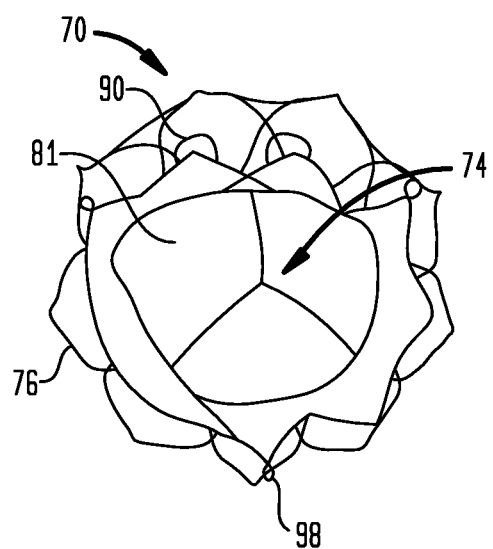
FIG. 3C is a view of the prosthetic heart valve of FIG. 3A from the outlet end.
Figure 3D:
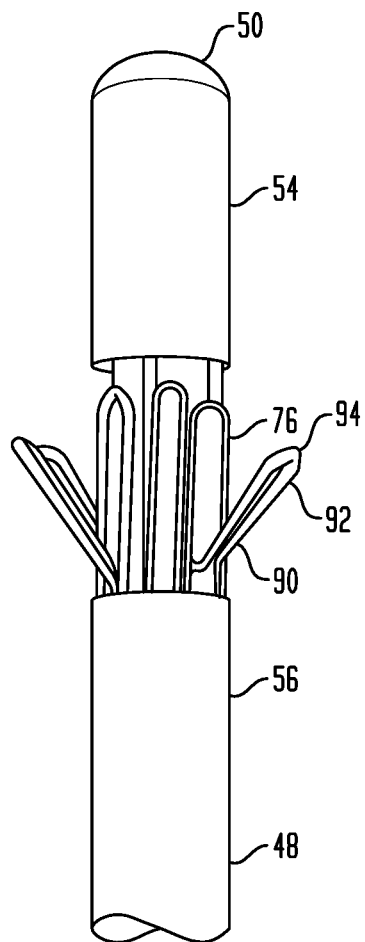
FIG. 3D is a side view of a distal portion of the delivery device of FIG. 1A with a self-expanding stent therein.
Figure 3E:
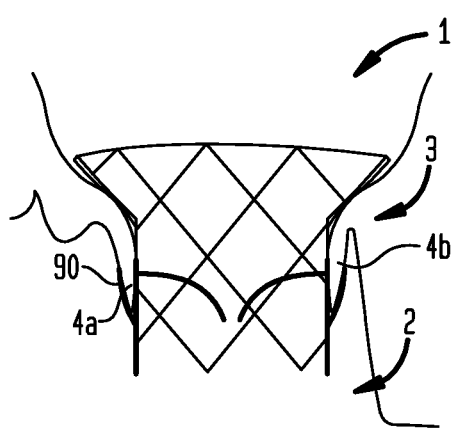
FIG. 3E is a schematic longitudinal cross-sectional view of the prosthetic heart valve of FIG. 3A deployed in the mitral valve annulus of a patient.

Blood flows through the mitral valve from the left atrium 1 to the left ventricle 2 (FIG. 3E). As used herein, the term "inflow end," when used in connection with a prosthetic mitral heart valve, refers to the end of the heart valve closest to the left atrium when the heart valve is implanted in a patient, whereas the term "outflow end," when used in connection with a prosthetic mitral heart valve, refers to the end of the heart valve closest to the left ventricle when the heart valve is implanted in a patient. Further, when used herein with reference to a delivery device, the terms "proximal" and "distal" are to be taken as relative to a user operating the device in an intended manner "Proximal" is to be understood as relatively close to the user and "distal" is to be understood as relatively farther away from the user. Also, as used herein, the terms "substantially," "generally," and "about" are intended to mean that slight deviations from absolute are included within the scope of the term so modified.

Referring now to FIGS. 1A and 1B, an exemplary delivery device 10 for use in delivering and deploying a collapsible prosthetic heart valve (or other types of self-expanding collapsible stents) in a patient is shown. Generally, the delivery device 10 includes a handle 12, an actuator assembly 14, and a catheter assembly 16. The catheter assembly 16 may function to deliver the prosthetic heart valve to and deploy the heart valve at a target location. The actuator assembly 14 may function to control deployment of the valve from the catheter assembly 16. The handle 12 may function to facilitate operation of the other components by a user. Each of these components is described in greater detail below. An exemplary method of use of the delivery device 10 and further structural details of the catheter assembly 16 are shown and described in the co-owned and co-pending U.S. Patent Application Publication No. 2014/0371844, the disclosure of which is hereby incorporated herein by reference.

As illustrated in FIG. 1A, the handle 12 includes a distal housing portion 20, an intermediate housing portion 21, and a proximal housing portion 22. The housing portions 20, 21, and 22 may be individual pieces configured to be joined to one another by knobs 36 and 37 as shown in FIG. 1A. Each of the housing portions 20, 21, and 22 may comprise a plurality of pieces including some combination of mating features, such as pegs and corresponding holes, to facilitate connecting the pieces together. The pieces of each of the housing portions 20, 21, and 22 may be connected to one another in any other suitable manner, including, for example, by fasteners, ultrasonic welding, or an adhesive.

Referring now to FIGS. 2A-2D, the housing portions 20, 21, and 22, and the knobs 36 and 37, individually or collectively, define a number of spaces for housing components of the actuator assembly 14 and the catheter assembly 16. For example, the housing portions 20, 21, and 22, and the knobs 36 and 37 define an elongated space in the handle 12 in which an inner lead screw 30 and an outer lead screw 32 are positioned and through which the lead screws may translate. (The inner and outer lead screws 30, 32 may alternatively be referred to in this disclosure as first and second lead screws 30, 32.) The distal housing portion 20 may also include an elongated slot 24a oriented in the longitudinal direction of the handle 12 through which a flush port 24b may extend, and the proximal housing portion 22 may include transverse openings 24c through which bosses 60a, 60b of a control member 62 may extend (FIGS. 4A-4G). Similarly, the housing portions 20, 21, and 22 may define generally circular recesses 20a, 21a, 21b, and 22a in which generally circular flanges 36a and 36b of the distal knob 36, and generally circular flanges 37a and 37b of the proximal knob 37 are positioned, respectively. Finally, the proximal housing portion 22 may include a flush aperture 28 sized to receive a flush port on a flush adapter 38 of the catheter assembly 16.

The distal knob 36 is rotationally coupled to each of the distal and intermediate housing portions 20, 21. The distal knob 36 has a first flange 36a disposed within the recess 20a of the distal housing portion 20 (FIG. 2C), and a second flange 36b disposed within the recess 21a of the intermediate housing portion 21. The pieces of the distal and intermediate housing portions 20 and 21 may be assembled around the flanges 36a, 36b so that the distal knob 36 is translationally fixed to the each of the housing portions 20, 21, but is free to rotate relative to the housing portions about the longitudinal axis of the handle 12.

The proximal knob 37 is rotationally coupled to each of the intermediate and proximal housing portions 21, 22. The proximal knob 37 has a first flange 37a disposed within the recess 21b of the intermediate housing portion 21, and a second flange 37b disposed within the recess 22a of the proximal housing portion 22. The pieces of the housing portions 21 and 22 may be assembled around the flanges 37a, 37b so that the proximal knob 37 is translationally fixed to the each of the housing portions 21, 22, but is free to rotate relative to the housing portions about the longitudinal axis of the handle 12.

The inner lead screw 30 extends within the elongated space in the handle 12 and through a central bore in each of the knobs 36, 37 sized to receive the inner lead screw. The central bore in the distal knob 36 may be internally threaded and configured to mate with external threads on the inner lead screw 30. The inner lead screw 30 always remains in threaded engagement with the distal knob 36. As the distal knob 36 is longitudinally confined relative to the housing portions 20, 21, and 22, rotation of the distal knob causes the inner lead screw 30 to translate proximally or distally within the handle 12, depending on the direction of rotation. Although the inner lead screw 30 may also extend through the central bore of the proximal knob 37, it is not functionally coupled to the proximal knob, such that rotation of the proximal knob does not move the inner lead screw. The inner lead screw 30 may be sized to have a predetermined travel distance within the elongated space of the handle 12 to provide limits to the travel range of the proximal segment 56 of the distal sheath 48, which will be described below. The distal knob 36 may have a textured outer circumference, such as a plurality of spaced ridges, to assist the user in gripping and rotating the distal knob.

The flush port 24b may be affixed to the inner lead screw 30 at an aperture 34 and may extend into the elongated slot 24a. The length of the elongated slot 24a may provide limits on the distance that the flush port 24b and, hence, the inner lead screw 30, may translate proximally or distally within the handle 12. As can be seen in FIG. 2D, the inner lead screw 30 has a lower longitudinal slot 30a configured to slidably engage with a longitudinal rib 20r located within the elongated space of the distal housing portion 20. The engagement of the rib 20r in the slot 30a prevents the inner lead screw 30 from simply rotating with the distal knob 36 and keeps the inner lead screw aligned in the longitudinal direction of the handle 12.

The outer lead screw 32 extends within the elongated space in the handle 12 and through a central bore in the proximal knob 37 sized to receive the outer lead screw. A longitudinal bore in the outer lead screw 32 is sized to receive the inner lead screw 30. The central bore in the proximal knob 37 may be internally threaded and configured to mate with external threads on the outer lead screw 32. The outer lead screw 32 always remains in threaded engagement with the proximal knob 37. As the proximal knob 37 is longitudinally confined relative to the housing portions 20, 21, and 22, rotation of the proximal knob causes the outer lead screw 32 to translate proximally or distally within the handle 12, depending on the direction of rotation. While the outer lead screw 32 may partially extend into an unthreaded portion of the central bore of the distal knob 36 when it is in its distalmost position, it is not functionally coupled to the distal knob, such that rotation of the distal knob does not move the outer lead screw. The outer lead screw 32 may be sized to have a predetermined travel distance within the elongated space of the handle 12 to provide limits to the travel range of the distal segment 54 of the distal sheath 48, which will be described below. The proximal knob 37 may have a textured outer circumference, such as a plurality of spaced ridges, to assist the user in gripping and rotating the proximal knob.

Figures 2A, 2B:
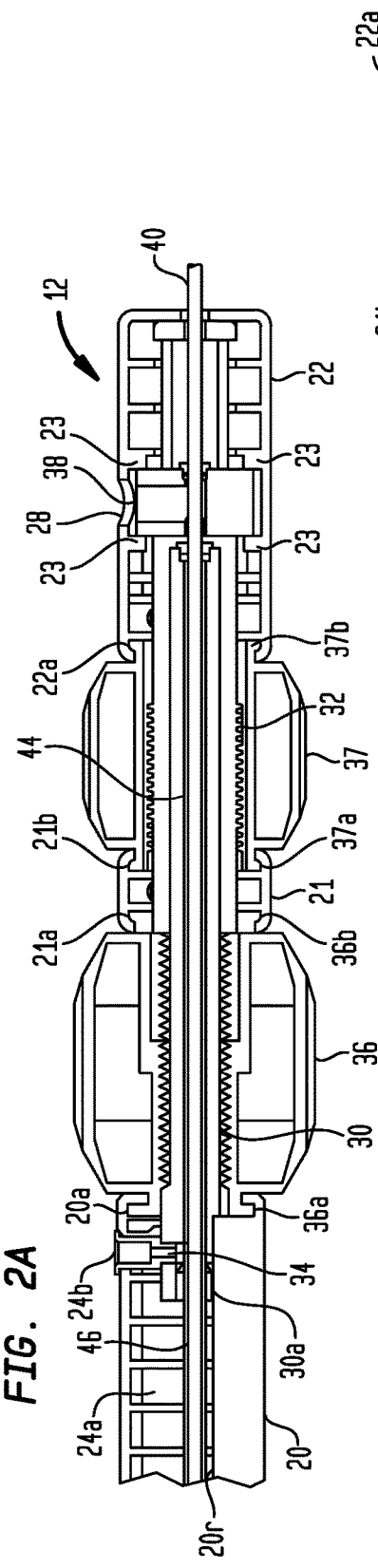
FIG. 2A is an enlarged longitudinal cross-section of a portion of the operating handle of FIG. 1A.
FIG. 2B is an enlarged longitudinal cross-section of a portion of the operating handle of FIG. 1A, shown in a perspective view.
Figure 2C:
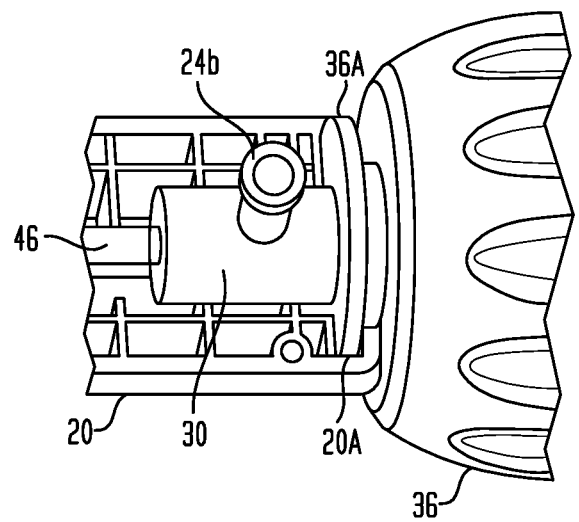
FIG. 2C is a perspective view a portion of the operating handle of FIG. 1A with a portion of the housing removed.
Figure 2D:
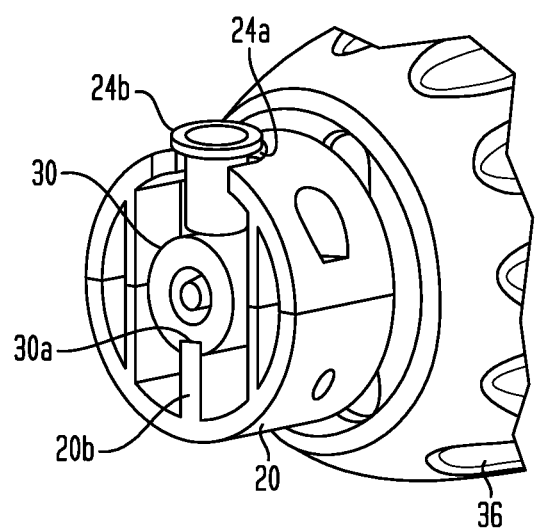
FIG. 2D is an enlarged lateral cross-section of a portion of the operating handle of FIG. 1A, shown in a perspective view.
Figure 8A:
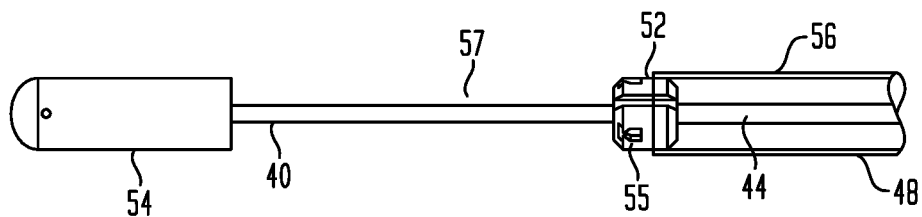
FIG. 8A is a partially transparent side view of a portion of the catheter assembly shown in FIG. 1A, with the proximal segment of the distal sheath in a fully-retracted position and the distal segment of the distal sheath in the fully-extended position.
Figure 8B:
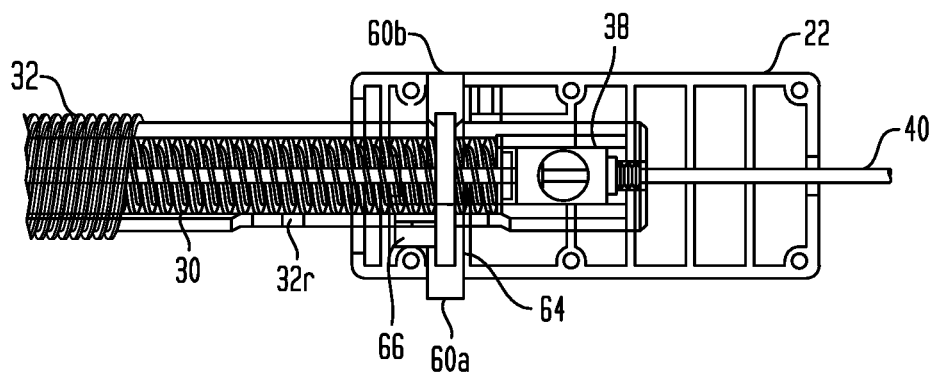
FIG. 8B is an enlarged top view of a portion of the operating handle of FIG. 1A with portions of the housing removed, with the outer lead screw being shown as partially transparent, and with the positions of the inner and outer lead screws corresponding to the positions of the distal and proximal segments of the distal sheath shown in FIG. 8A.
Figure 8C:
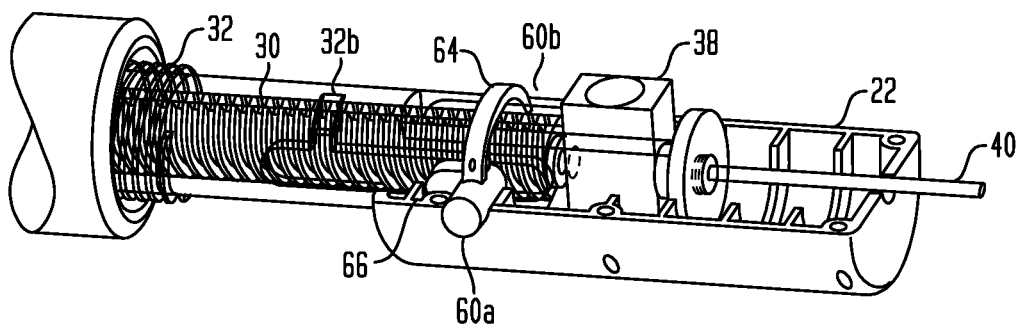
FIG. 8C is an enlarged perspective view of a portion of the operating handle of FIG. 1A with portions of the housing removed, with the outer lead screw being shown as partially transparent, and with the positions of the inner and outer lead screws corresponding to the positions of the distal and proximal segments of the distal sheath shown in FIG. 8A.

As can be seen in FIGS. 2A and 2B, although the portion of the inner lead screw 30 that extends within the outer lead screw 32 may be threaded, the longitudinal bore of the outer lead screw is not threaded, so the inner lead screw is freely slidable within the longitudinal bore of the outer lead screw. The outer lead screw 32 includes an elongated slot 32v sized to receive the flush adapter 38 (FIGS. 4A-4G). The engagement of the flush adapter 38 with locating tabs 23 in the proximal housing portion 22 of the handle 12 fixes the location and orientation of the flush adapter and a retaining element 52 in the catheter assembly 16 (to be described below) relative to the handle, prevents the outer lead screw from rotating within the proximal housing portion of the handle and keeps the outer lead screw aligned in the longitudinal direction of the handle. The length of the elongated slot 32v in the outer lead screw 32 and the engagement of the flush adapter 38 therein may limit the distance that the outer lead screw may translate proximally or distally within the handle 12. The flush adapter 38 may also act as a stop limit the proximal translation of the inner lead screw 30 within the longitudinal bore of the outer lead screw 32 (FIGS. 8B and 8C).

The inner lead screw 30 has an upper longitudinal slot 30b which, along with the lower longitudinal slot 30a, are configured to slidably engage with respective upper and lower longitudinal ribs 32b and 32a located within the longitudinal bore of the outer lead screw 32. The engagement of the ribs 32a, 32b in the slots 30a, 30b prevents the inner lead screw 30 and the distal housing portion 20 from simply rotating with the distal knob 36 relative to the proximal housing portion 22, and keeps the inner lead screw aligned in the longitudinal direction with the outer lead screw 32. The engagement of the ribs 32a, 32b with the slots 30a, 30b rotationally lock the inner lead screw 30 to the outer lead screw 32, but each of the lead screws is independently longitudinally slidable relative to the other of the lead screws.

An inner shaft 40 of the catheter assembly 16 is also illustrated in FIGS. 1A through 2B. The inner shaft 40 may extend from beyond a proximal end of the handle 12, through the handle subassembly, to a distal portion of delivery device 10 (the distal portion is described in greater detail below). In particular, the inner shaft 40 may extend from a hub 42 on its proximal end through the inner and outer lead screws 30, 32 and the flush adapter 38, and to the distal portion of the delivery device 10. The hub 42 may be positioned proximally of the proximal end of handle 12 such that, during use, a user may grasp the proximal hub. The inner shaft 40 and the hub 42 may have an internal lumen configured to receive a guide wire that may extend completely through the delivery system 10 from the hub at the proximal end of the delivery system to a distal tip 50 at the distal end of the delivery system. The hub 42 may be a luer configured to permit flushing of the internal lumen of the shaft 40.

FIGS. 1A through 2B illustrate additional components of the catheter assembly 16. In general, the catheter assembly 16 includes the inner shaft 40, described in part above, an inner sheath 44, a middle sheath 46, and a distal sheath 48. The distal sheath 48 may have a distal segment 54 and a proximal segment 56, described more fully below.

The inner shaft 40 extends from the hub 42 to an atraumatic distal tip 50. The inner shaft 40 is fixedly attached to the hub 42 and the distal tip 50, and the distal tip is fixedly attached to the distal segment 54. The inner shaft 40 is removably attached to the outer lead screw 32 via mating threads, so that the user may disengage the outer lead screw from the inner shaft and may selectively push or pull the hub 42 distally or proximally, as will be described in greater detail below. When the inner shaft 40 is attached to the outer lead screw 32, proximal or distal translation of the outer lead screw causes corresponding translation of the inner shaft as well as the distal segment 54 of the distal sheath 48, to which the inner shaft is connected.

The inner sheath 44 is positioned over the inner shaft 40 and extends from the flush adapter 38, through the knobs 36, 37 and the inner and outer lead screws 30, 32, and terminates at the retaining element 52 in the catheter assembly 16. The inner sheath 44 is fixedly attached to the flush adapter 38 and the retaining element 52. The location and orientation of the inner sheath 44 are fixed with respect to the handle 12 due, at least in part, to its connection to the flush adapter 38, which is held in a fixed position by locating tabs 23 in the proximal housing portion 22 of the handle 12.

The middle sheath 46 is positioned over the inner sheath 44 and the inner shaft 40, and extends from the distal end of the inner lead screw 30 to the proximal end of the distal sheath 48. The middle sheath 46 is fixedly attached to both the inner lead screw 30 and the proximal end of the distal sheath 48 such that proximal or distal translation of the inner lead screw causes corresponding translation of the middle sheath as well as the proximal segment 56 of the distal sheath to which the middle sheath is connected.

The distal sheath 48 is positioned over the inner sheath 44 and the inner shaft 40, and extends from the distal end of the middle sheath 46 to the atraumatic distal tip 50. The tip 50 may be blunt to facilitate advancement of the delivery device 10 in the body of the patient without injury to the patient's tissue. For example, the tip 50 may have a rounded distal surface that faces away from the distal sheath 48. The distal segment 54 of the distal sheath 48 may be coupled to the tip 50 so that translation of the inner shaft 40 (for example, by a user rotating the proximal knob 37) results in a corresponding translation of the distal segment. The proximal segment 56 of the distal sheath 48 may be coupled to the middle sheath 46, so that translation of the middle sheath (for example, by a user rotating the distal knob 36) results in a corresponding translation of the proximal segment. In some embodiments, the tip 50 and/or the distal segment 54 of the distal sheath 48 may be made of a material that limits reflection under echocardiographic imaging.

The distal segment 54 and the proximal segment 56 may include complementary releasable coupling features such as ribs and/or overlapping portions, which may permit the distal and proximal segments to align concentrically when they are brought together to cover a compartment 57 configured to house a prosthetic heart valve. In one example, the proximal end 58 of the distal segment 54 may be slightly smaller in diameter than the distal end 59 of the proximal segment 56 (or vice versa) such that these ends may mate with one another in an overlapping concentric relationship.

The space between the retaining element 52 and the distal tip 50 defines the compartment 57 for housing a prosthetic heart valve. Specifically, a prosthetic heart valve may be disposed about the inner shaft 40 in the compartment 57 and covered by the distal sheath 48. The retaining element 52 may include a plurality of recesses 55 distributed circumferentially around its perimeter, the recesses being configured to accept retainers disposed near the outflow end of the prosthetic heart valve, as will be described in more detail below. The distal segment 54 and the proximal segment 56 of the distal sheath 48 may be translatable relative to one another to form an increasing gap G therebetween (FIG. 1A) so as to expose the prosthetic heart valve in the compartment 57 for deployment. Further description of the aforementioned structural details of the catheter assembly 16 is provided in the co-owned and co-pending U.S. Patent Application Publication No. 2014/0371844, the disclosure of which is hereby incorporated herein by reference.

The proximal and distal translation of the distal segment 54 and the proximal segment 56 of the distal sheath 48 to deploy a prosthetic heart valve can be controlled by manual operation of the handle 12 by a user. The distal knob 36 is always in threaded engagement with the inner lead screw 30, which is coupled to the proximal segment 56 via the middle sheath 46, such that rotation of the distal knob by a user will translate the proximal segment in the longitudinal direction of the catheter assembly 16. The proximal knob 37 is always in threaded engagement with the outer lead screw 32, which is coupled to the distal segment 54 via the inner shaft 40, such that rotation of the proximal knob by a user will translate the distal segment in the longitudinal direction of the catheter assembly 16.

The threads of the inner and outer lead screws 30, 32 are shown in the figures as being oriented in opposite directions from one another. This can be seen in FIGS. 5B, 6B, 6C, 7B, 8B, and 8C. The thread pitch of the inner and outer lead screws 30, 32 may be close to one another so that they travel similar distances upon a similar degree of rotation of the knobs 36, 37, or the thread pitch of the inner screw may be greater or less than the thread pitch of the outer screw to accommodate alternative designs of the collapsible prosthetic heart valve or other implantable medical devices to be deployed into a patient. The thread pitch of the inner and outer lead screws 30, 32 may also be selected based on the desired speed of deployment of the corresponding portions of the prosthetic heart valve to be delivered by the delivery device 10, that is, the desired amount of longitudinal translation of the proximal and distal segments 56, 54 for a given degree of rotation of the corresponding distal and proximal knobs 36, 37.

FIGS. 3A-3C show a collapsible prosthetic heart valve 70 in an expanded condition after being released from the compartment 57 of the delivery device 10 by the distal movement of the distal segment 54 of the distal sheath 48 relative to the prosthetic heart valve and/or the proximal movement of the proximal segment 56 of the distal sheath relative to the prosthetic heart valve. The collapsible prosthetic heart valve 70 is designed to replace the function of the native mitral valve of a patient. The prosthetic heart valve 70 has an inflow end 72 and an outflow end 74. The prosthetic heart valve 70 may be generally cylindrically shaped in the expanded condition and may include features for anchoring to native heart tissue, as will be discussed in more detail below. Throughout this disclosure, a prosthetic mitral valve is used as an exemplary valve to be loaded into a delivery device such as the delivery device 10. However, the delivery device 10 described herein may be used to deliver other collapsible valves, e.g., a collapsible prosthetic aortic valve, other collapsible stents, or other collapsible medical devices.

The prosthetic heart valve 70 may include a stent 76, which may be formed from biocompatible materials that are capable of self-expansion, such as, for example, shape-memory alloys including Nitinol. The stent 76 may include a plurality of struts 78 that form closed cells 80 connected to one another in one or more annular rows around the stent. The cells 80 may all be of substantially the same size around the perimeter and along the length of the stent 76. Alternatively, the cells 80 near the inflow end 72 of the prosthetic valve 70 may be larger or smaller than the cells near the outflow end 74 of the valve. The stent 76 may be expandable to provide a radial force to assist with positioning and stabilizing the prosthetic heart valve 70 within the native mitral valve annulus of the patient.

The prosthetic heart valve 70 may also include a valve assembly disposed within the stent 76. The valve assembly may include a plurality of leaflets 81 attached to a cylindrical cuff 82. The leaflets may replace the function of the native mitral valve leaflets. That is, the leaflets coapt with one another to function as a one-way valve. The prosthetic heart valve 70 may have two or more leaflets when used to replace the mitral valve or other cardiac valves within a patient. The valve assembly of the prosthetic heart valve 70 may be substantially cylindrical in the expanded condition. Both the cuff 82 and the leaflets 81 may be wholly or partly formed of any suitable biological material, such as bovine or porcine pericardium, or polymers, such as polytetrafluoroethylene (PTFE), urethanes and the like. The valve assembly may be secured within the interior of the stent 76 by suturing to the struts 78 or by using tissue glue, ultrasonic welding, or other suitable attachment methods.

Referring to FIGS. 3D and 3E, the prosthetic heart valve 70 may include additional securement features in the form of anchor arms 90 that hook under native mitral valve leaflets 4a, 4b to help prevent the prosthetic heart valve from migrating into the left atrium 1. The anchor arms 90 may each be formed of a single wire 92 bent or otherwise formed into a body portion. The wire 92 is preferably a shape-memory alloy such as Nitinol, so that when the prosthetic heart valve 70 is deployed from the delivery device 10, the stent 76 automatically radially expands to the shape shown in FIG. 3A, and the tips 94 of the anchor arms 90 automatically extend away from the stent 76. In one example, the wire 92 is a Nitinol wire having a diameter of about 0.015 inches (0.38 mm). In the example shown in FIG. 3A, each anchor arm 90 is formed of a looped or bent wire 92 having a rounded or blunted central tip 94. In other embodiments, each anchor arm may be formed of a single wire extending to a free tip, or other configurations and/or shapes of anchor arms may be used.

Each anchor arm 90 may extend away from the struts 78 so that the tip 94 of the anchor arm lies at a spaced distance radially outward from the struts 78. Preferably, the tip 94 of each anchor arm 90 is blunt and/or rounded to reduce the likelihood of the tips damaging the native tissue hooked by the anchor arms. In addition or alternatively, a blunted and/or rounded end cap may be assembled over or onto the tips 94 and fixed in place, for example by welding, to provide an atraumatic tissue contact surface. Other exemplary types of self-expanding prosthetic heart valves 70 and further structural details thereof are shown and described in the co-owned and co-pending U.S. Patent Application Publication No. 2016/0278923, the disclosure of which is hereby incorporated herein by reference.

Figure 5A:
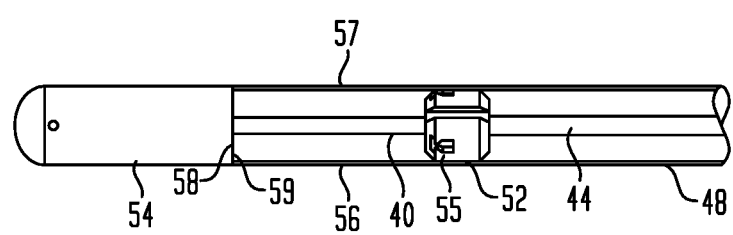
FIG. 5A is a partially transparent side view of a portion of the catheter assembly shown in FIG. 1A, with the distal and proximal segments of the distal sheath each in a fully-closed position.

The prosthetic heart valve 70 may also include a number of retainers 98 extending from the outflow end 74 of the stent 76. Among other things, the retention of the retainers 98 in the recesses 55 (FIG. 5A) of the retaining element 52 prevents the outflow end 74 of the prosthetic heart valve 70 from being inadvertently or unintentionally deployed from the proximal segment 56 of the distal sheath 48. The retention of the retainers 98 in the recesses 55 of the retaining element 52 also serves to fix the rotational orientation of the prosthetic heart valve 70 relative to the handle 12, which may provide the user with the ability to have a consistent rotational orientation of the valve during deployment, so that for valves having different anterior and posterior sides, the valve can be delivered to the native annulus of a patient with the proper rotational orientation relative to the native annulus. During the deployment of the prosthetic heart valve 70 from the compartment 57, a user may rotate the knob 36 in a first direction, thereby moving the inner lead screw 30, the middle sheath 46, and the proximal segment 56 of the distal sheath 48 in a proximal direction. This proximal movement of the proximal segment 56 relative to the prosthetic heart valve 70 exposes the retainers 98 and allows them to disengage from the recesses 55 of the retaining element 52. Once disengaged from the retaining element 52, the prosthetic heart valve 70 may fully deploy into the patient.

FIGS. 4A-4G illustrate components of a resheathing lock assembly of the handle 12. The resheathing lock assembly includes a control member 62 that may be mounted around the outer lead screw 32. The control member 62 may have a ring 64 extending around the outer lead screw 32 proximally of the proximal knob 37, and a protuberance 66 that extends into and through an elongated slot 32h extending longitudinally in outer lead screw 32. The control member 62 is constrained from longitudinal movement relative to the proximal housing portion 22 by the engagement of the bosses 60a, 60b in the transverse openings 24c (FIG. 4D) in the proximal housing portion. The control member 62 is also constrained by lateral fins 20f from flexing and/or twisting when the proximal end of the inner lead screw 30 contacts the protuberance 66, as will be described below.

The control member 62 can be actuated by a user pressing on one of the bosses 60a, 60b that extend out from the proximal housing portion 22 through one of the transverse openings 24c. When the control member 62 is in an unlocked position shown in FIGS. 4A-4C, a first one of the bosses 60a projects out of the respective transverse opening 24c (FIG. 4C), where it is available to be depressed by the user. When the control member 62 is in a locked position shown in FIGS. 4E-4G, a second one of the bosses 60b projects out of the respective transverse opening 24c (FIG. 4G), where it is available to be depressed by the user. When a user depresses the boss 60a or the boss 60b, the control member 62 slides laterally within the proximal housing portion 22.

Figure 4A:
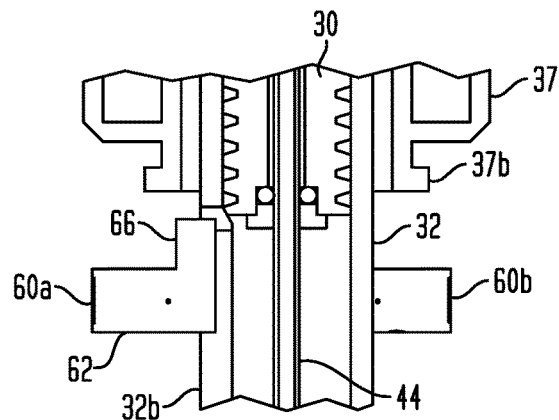
FIG. 4A is an enlarged longitudinal cross-section of a portion of the operating handle of FIG. 1A with the housing removed and the resheathing lock in an unlocked position.
Figure 4B:
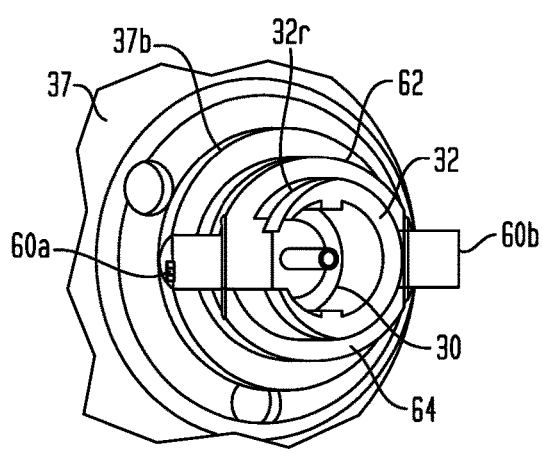
FIG. 4B is an enlarged lateral cross-section, shown in a perspective view, of a portion of the operating handle of FIG. 1A with the housing removed and the resheathing lock in the unlocked position.
Figure 4C:
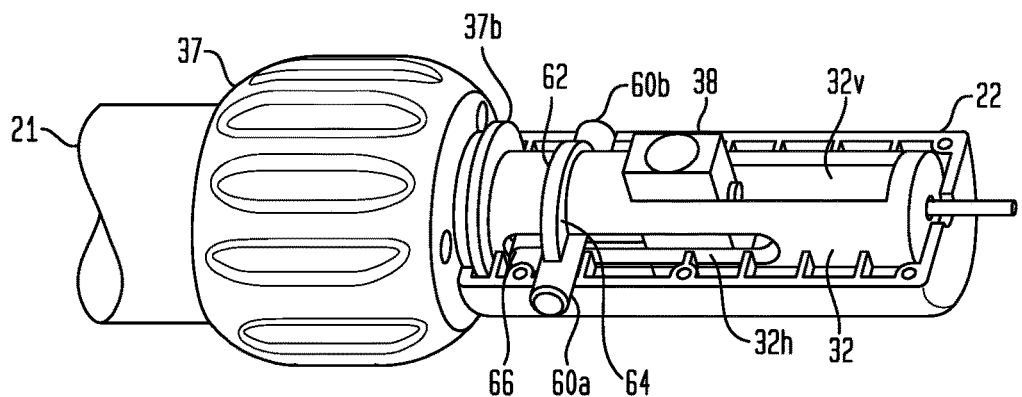
FIG. 4C is a perspective view a portion of the operating handle of FIG. 1A with a portion of the housing removed and the resheathing lock in the unlocked position.
Figure 4D:
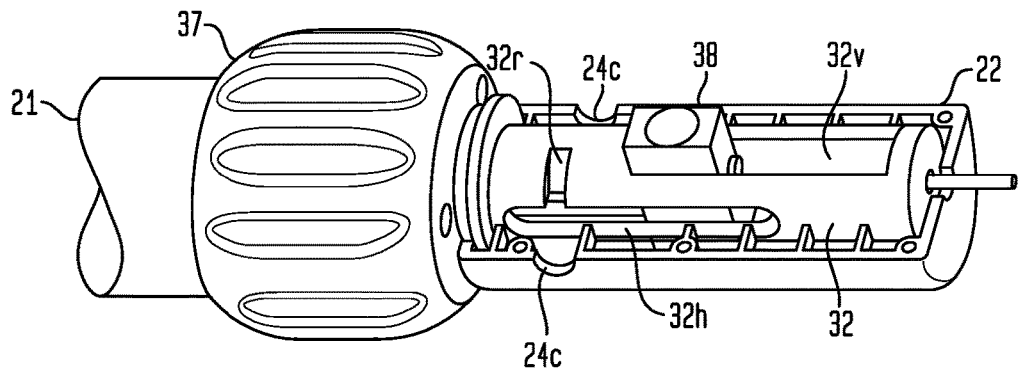
FIG. 4D is a perspective view a portion of the operating handle of FIG. 1A with a portion of the housing and the resheathing lock removed.

When the control member 62 is in the unlocked position shown in FIGS. 4A-4C, the protuberance 66 does not extend through the slot 32h and into the bore of the outer lead screw 32, so there is no interference between the protuberance and the proximal end of the inner lead screw 30, and the inner lead screw is not prevented from continued proximal movement. Also in this unlocked position, the ring 64 of the control member 62 does not extend into a recess 32r that is defined in the outer surface of the outer lead screw 32 and sized to selectively receive a portion of the ring, and the outer lead screw is not prevented from distal movement. It should be noted that, when in the position shown in FIGS. 4C and 4D, the outer lead screw 32 is prevented from moving proximally by the position of the flush adapter 38 at the distal end of the slot 32v.

Figure 4E:
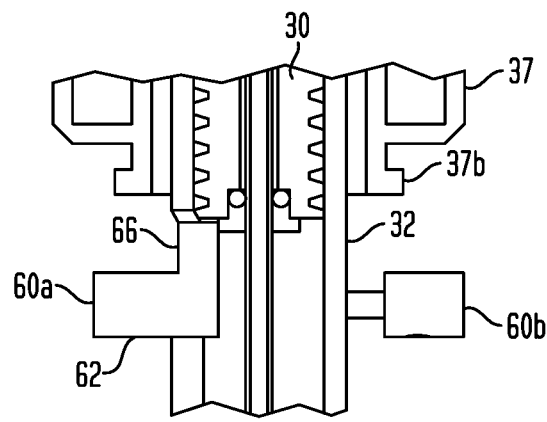
FIG. 4E is an enlarged longitudinal cross-section of a portion of the operating handle of FIG. 1A with the housing removed and the resheathing lock in a locked position.
Figure 4F:
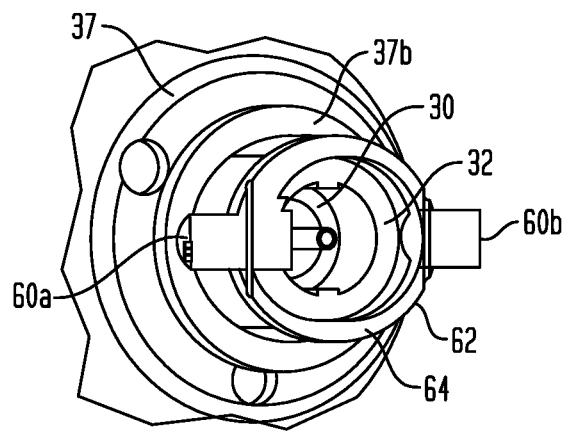
FIG. 4F is an enlarged lateral cross-section, shown in a perspective view, of a portion of the operating handle of FIG. 1A with the housing removed and the resheathing lock in the locked position.
Figure 4G:
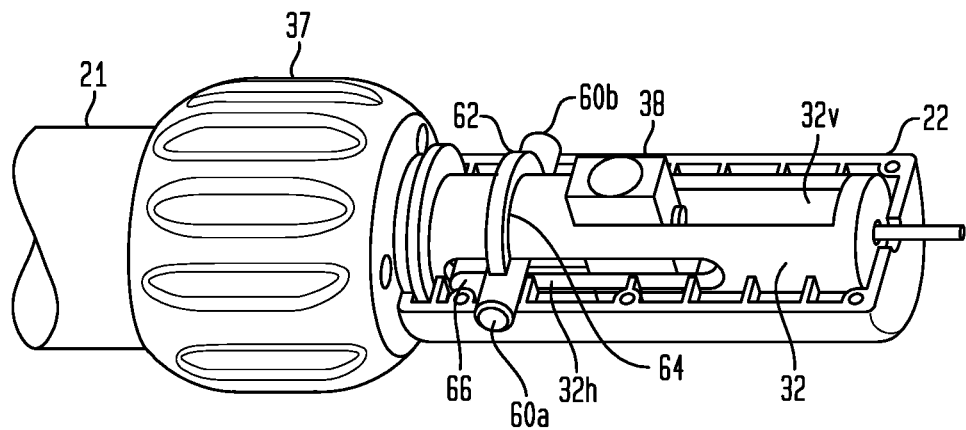
FIG. 4G is a perspective view a portion of the operating handle of FIG. 1A with a portion of the housing removed, with the resheathing lock shown in the locked position.

When the control member 62 is in the locked position shown in FIGS. 4E-4G, the protuberance 66 extends through the slot 32h and into the bore of the outer lead screw 32, so there is interference between the protuberance and the proximal end of the inner lead screw 30, and the inner lead screw is prevented from proximal movement beyond the position of the protuberance. The selective interference between the protuberance 66 and the proximal end of the inner lead screw 30 may function as a resheathing lock adapted to temporarily limit the proximal movement of the proximal segment 56 of the distal sheath 48. This limitation on the proximal movement of the proximal segment 56 will ensure that the retainers 98 of the prosthetic valve 70 remain captured between the recesses 55 of the retaining element 52 and the proximal segment while the anchor arms 90 are released from the proximal segment, thereby preventing the user from completing the deployment of the prosthetic valve 70 when unintended. The initial distance that the proximal segment 56 of the distal sheath 48 can travel before being limited by the control member 62 may depend on the structure of the particular prosthetic valve to be deployed. In the example shown in the figures, the initial travel distance of the proximal segment 56 is about 9 mm less than the amount of travel needed to fully expose the retainers 98 of the prosthetic valve 70, although the initial travel distance of the proximal segment may vary depending on the particular delivery device design and the particular prosthetic valve being deployed.

When the control member 62 is in the locked position, a portion of the ring 64 extends into the recess 32r in the outer lead screw 32, so there is interference between the ring and the outer lead screw, and the outer lead screw is prevented from moving distally. The selective interference between the ring 64 and the recess 32r in the outer lead screw 32 may function as a deployment lock adapted to temporarily prevent any movement of the distal segment 54 of the distal sheath 48. This limitation on the distal movement of the distal segment 54 will ensure that the inflow end 72 of the prosthetic heart valve 70 remains captured by the distal segment of the distal sheath 48, thereby preventing the user from beginning deployment of the inflow end of the prosthetic heart valve when unintended.

The control member 62 and the proximal housing portion 22 may include a ball/detent feature (not shown) that retains the control member in the locked position until sufficient force is applied by the user onto the boss 60b to overcome the interference between the ball and the detent. The ball may be biased to remain engaged into the detent by a spring element. The ball/detent feature may be replaced by any variation that retains the control member in the locked position until sufficient force is applied by the user onto the boss 60b. Requiring sufficient force to be applied by the user to move the control member 62 from the locked position to the unlocked position may prevent accidental user actuation of the control member by unintended contact with the boss 60b, and such a ball/detent feature may provide tactile feedback during actuation of the control member, since a user may feel the ball popping out of the detent as the boss 60b is depressed.

The operation of the delivery device 10 to deploy the prosthetic heart valve 70 will now be described with reference to FIGS. 5A through 8C. In a typical procedure to deploy the prosthetic heart valve 70 in a patient, the valve may be maneuvered to the implantation site using a transapical approach, as would readily be known to one having ordinary skill in the art. Briefly, the user would insert the distal end of the delivery device 10 through an intercostal space between the patient's ribs and through the apex of the patient's heart and the left ventricle to the mitral valve annulus, where the prosthetic heart valve 70 would be deployed. Echocardiographic imaging, e.g., intracardiac echocardiography (ICE), transesophageal echocardiography (TEE), or transthoracic echocardiography (TTE), may be used to visualize the position of the distal end of the delivery device 10 during deployment of the valve 70.

To load the delivery device 10 with a collapsible prosthetic valve 70, the user may place the control member 62 in the unlocked position with the first boss 60a projecting out of its transverse opening 24c, which can be seen in FIGS. 8B and 8C. In this position, the ring 64 does not extend into the recess 32r in the outer lead screw 32, so the outer lead screw may be moved to its distalmost position by rotating the proximal knob 37 in a first direction, which will move the distal segment 54 of the distal sheath 48 to its distalmost position (FIG. 8A). Also in this position, the protuberance 66 does not extend into the bore of the outer lead screw 32, so the inner lead screw 30 may be moved to its proximalmost position by rotating the distal knob 36 in a first direction. This will expose the maximum amount of the compartment 57 for compressing and loading of the prosthetic valve 70, which may be accomplished, for example, using the mitral valve loading tool shown and described in the co-owned and co-pending U.S. Patent Application Publication No. 2016/0270914, the disclosure of which is hereby incorporated herein by reference.

Figure 5B:
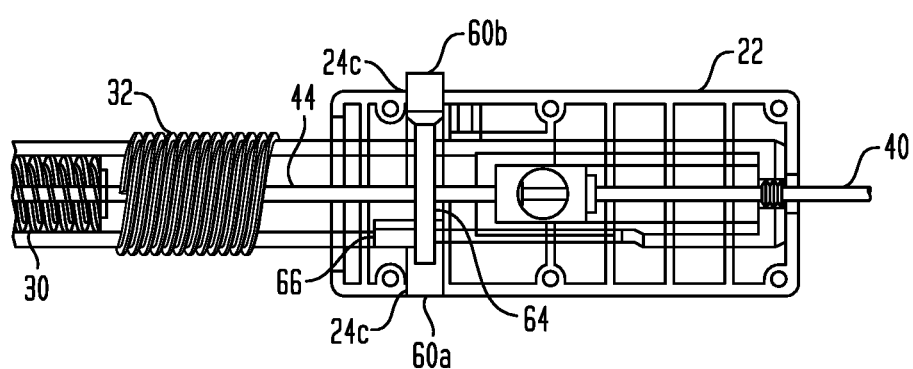
FIG. 5B is an enlarged top view of a portion of the operating handle of FIG. 1A with portions of the housing removed, with the outer lead screw being shown as partially transparent, and with the positions of the inner and outer lead screws corresponding to the positions of the distal and proximal segments of the distal sheath shown in FIG. 5A.

To cover the compartment 57 with the distal sheath 48 to hold the prosthetic valve 70 in the compressed state (FIG. 5A), the distal segment 54 of the distal sheath 48 may be moved to its proximalmost position by rotating the proximal knob 37 in a second direction, which will move the outer lead screw 32 to its proximalmost position (FIG. 5B). Also, the proximal segment 56 of the distal sheath 48 may be moved to its distalmost position by rotating the distal knob 36 in a second direction, which will move the inner lead screw 30 to its distalmost position. When the distal sheath 48 completely covers the compartment 57, the distal end 59 of the proximal segment 56 will contact or overlap with the proximal end 58 of the distal segment 54. Once the compartment 57 is covered, the user may place the control member 62 in the locked position shown in FIG. 5A, with the second boss 60b projecting out of its transverse opening 24c. Placing the control member 62 in the locked position will move a portion of the ring 64 into the recess 32r in the outer lead screw 32, thereby preventing movement of the outer lead screw, and will move the protuberance 66 into the bore of the outer lead screw 32, thereby limiting movement of the inner lead screw 30 to prevent the compartment 57 from being fully uncovered.

Figure 6A:
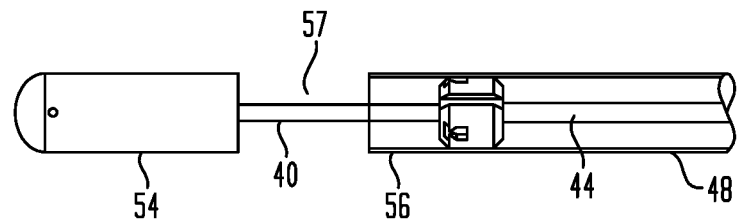
FIG. 6A is a partially transparent side view of a portion of the catheter assembly shown in FIG. 1A, with the proximal segment of the distal sheath in a partially-retracted position.
Figure 6B:
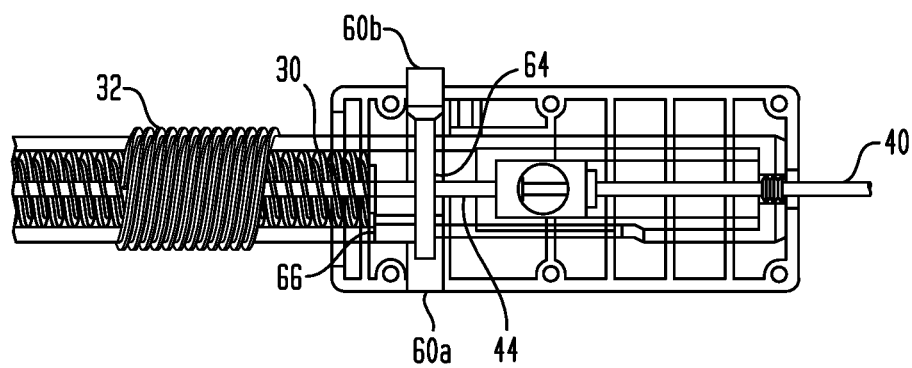
FIG. 6B is an enlarged top view of a portion of the operating handle of FIG. 1A with portions of the housing removed, with the outer lead screw being shown as partially transparent, and with the positions of the inner and outer lead screws corresponding to the positions of the distal and proximal segments of the distal sheath shown in FIG. 6A.

To use the operating handle 12 to deploy a prosthetic valve 70 that has been loaded into the compartment 57 and covered by the distal sheath 48, the user may insert the distal end of the delivery device 10 into a patient, and the compartment may be maneuvered to the target location, such as the native mitral valve annulus of the patient. To begin uncovering the prosthetic heart valve 70, the user may rotate the distal knob 36 in the first direction, which will move the inner lead screw 30, the middle sheath 46, and the proximal segment 56 of the distal sheath 48 proximally. The user may continue rotating the distal knob 36 in the first direction until the proximal end of the inner lead screw 30 contacts the protuberance 66, as can be seen in FIG. 6B. Moving the inner lead screw 30 proximally will move the proximal segment 56 proximally until the anchor arms 90 of the prosthetic heart valve 70 are uncovered and extend laterally away from the stent 76 to a position around the native mitral valve leaflets (e.g., as shown in FIG. 3E). At this point, the proximal segment 56 will be in the position shown in FIGS. 3D and 6A.

Figure 6C:
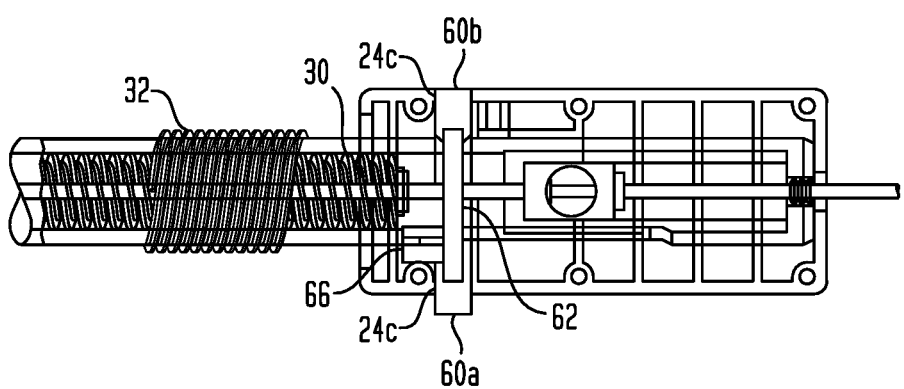
FIG. 6C is an enlarged top view of a portion of the operating handle of FIG. 1A with portions of the housing removed, with the outer lead screw being shown as partially transparent, and with the resheathing lock shown in the unlocked position.

Once the user is satisfied with the position of the anchor arms 90, the user may continue to deploy the prosthetic heart valve 70. To do so, the user may move the control member 62 to the unlocked position with the first boss 60a projecting out of its transverse opening 24c, as can be seen in FIG. 6C, thereby withdrawing the ring 64 from the recess 32r in the outer lead screw 32 and withdrawing the protuberance 66 from the inner bore of the outer lead screw.

Figure 7A:
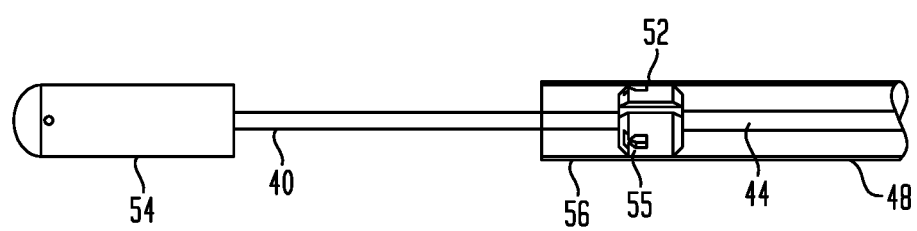
FIG. 7A is a partially transparent side view of a portion of the catheter assembly shown in FIG. 1A, with the proximal segment of the distal sheath in the partially-retracted position and the distal segment of the distal sheath in a fully-extended position.
Figure 7B:
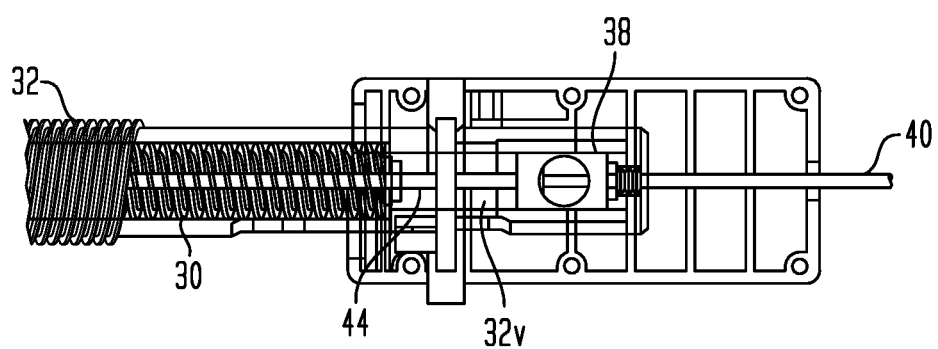
FIG. 7B is an enlarged top view of a portion of the operating handle of FIG. 1A with portions of the housing removed, with the outer lead screw being shown as partially transparent, and with the positions of the inner and outer lead screws corresponding to the positions of the distal and proximal segments of the distal sheath shown in FIG. 7A.

Then, the user may rotate the proximal knob 37 in the first direction, which will move the outer lead screw 32, the inner shaft 40, and the distal segment 54 of the distal sheath 48 distally. The user may continue rotating the proximal knob 37 in the first direction until the flush adapter 38 is contacted by the proximal end of the elongated slot 32v, as can be seen in FIG. 7B, thereby limiting the distal movement of the outer lead screw 32. Moving the outer lead screw 32 distally will move the distal segment 54 distally until the inflow end 72 of the prosthetic heart valve 70 is uncovered and fully radially expands. At this point, the distal segment 54 will be in the position shown in FIG. 7A, and the retainers 98 at the outflow end 74 of the prosthetic heart valve 70 will still be engaged in the recesses 55 of the retaining element 52, because the proximal segment 56 has not yet been moved to its proximalmost position.

Next, the user may rotate the distal knob 36 in the first direction, which will move the inner lead screw 30, the middle sheath 46, and the proximal segment 56 of the distal sheath 48 proximally. The user may continue rotating the distal knob 36 in the first direction until the proximal end of the inner lead screw 30 contacts the flush adapter 38, as can be seen in FIGS. 8B and 8C. Moving the inner lead screw 30 proximally will move the proximal segment 56 proximally until the prosthetic heart valve 70 is completely uncovered, expands, and separates from the delivery device 10. At this point, the proximal segment 56 will be in the position shown in FIG. 8A, and the compartment 57 will be completely uncovered.

Next, the user may remove the delivery device 10 from the patient. The user may re-close the compartment 57 so that the proximal end 58 of the distal segment 54 will contact or overlap with the distal end 59 of the proximal segment 56, thereby minimizing the risk that tissue of the patient becomes snagged on the distal segment 54 during withdrawal of the catheter assembly 16 from the patient. To re-close the compartment, the user may grasp and rotate the hub 42 (FIGS. 1A and 1B) relative to the handle 12 to unscrew the inner shaft 40 from the outer lead screw 32. (In other embodiments, the inner shaft 40 may be decoupled from the outer lead screw 32 via alternative mechanisms, such as a quick release lever, button, or the like.) Once the inner shaft 40 is decoupled from the outer lead screw 32, the user may pull the hub 42 proximally relative to the handle to freely slide the inner shaft proximally until the distal segment 54 contacts the proximal segment 56. Although the proximal segment 56 will be in its proximalmost position after deployment of the prosthetic heart valve 70, the inner shaft 40 can be pulled proximally by a sufficient distance to permit the distal segment 54 to contact the proximal segment, thereby closing the compartment 57. Once the compartment 57 is closed, the catheter assembly 16 may be withdrawn from the patient.

If, at any point during valve deployment, the user desires to resheathe the valve 70 while the valve is partially deployed, to either reposition the valve or withdraw the valve from the patient, the user may rotate the distal knob 36 in the second direction to move the proximal segment 56 of the distal sheath 48 to its distalmost position to completely cover the valve 70. The distal segment 54 of the distal sheath 48 may be moved proximally to contact the proximal segment 56 by a user rotating the proximal knob 37 in the second direction. Then, the distal end of the delivery device 10 may be repositioned within the native mitral valve annulus, and deployment of the valve may be reattempted, or the delivery device may be withdrawn from the patient. Once the proximal segment 56 of the distal sheath 48 to its distalmost position to completely cover the valve 70, it may be necessary to withdraw the delivery device 10 from the patient so that the inflow end 72 of the valve can be reloaded into the distal segment 54 of the distal sheath. Then, the distal end of the delivery device 10 may be reinserted into the patient and repositioned within the native mitral valve annulus, and deployment of the valve may be reattempted.

Although in the embodiments shown herein, a distal threaded knob 36 is configured to mate with an inner lead screw 30 to move a proximal segment 56 of a distal sheath 48, and a proximal threaded knob 37 is configured to mate with an outer lead screw 32 to move a distal segment 54 of the distal sheath, the invention contemplates other coupling mechanisms. For example, in other embodiments, the threaded knobs 36, 37 and the lead screws 30, 32 may be replaced with other coupling mechanisms such as a rack and pinion arrangement. Although, in the embodiments shown herein, a resheathing lock assembly includes a control member configured to translate laterally to temporarily interfere with the movement of the lead screws 30, 32, the invention contemplates other selective locking mechanisms. For example, in other embodiments, the resheathing lock may include a control member configured to rotate about a longitudinal axis of the handle 12 to temporarily interfere with the movement of the lead screws 30, 32.

Although, in the embodiments shown herein, the outer lead screw 32 has longitudinal ribs 32a, 32b that engage with respective longitudinal slots 30a, 30b in the inner lead screw, the invention contemplates other mechanisms for permitting the outer and inner lead screws to slide longitudinally relative to one another while being rotationally locked to one another. For example, in other embodiments, the inner lead screw may have one or more longitudinal ribs engaged in respective longitudinal slots in the outer lead screw. Although two ribs 32a, 32b are shown and described herein as being engaged in two respective longitudinal slots 30a, 30b, in other embodiments, the outer and inner lead screws 32, 30 may be rotationally locked to one another by any number of longitudinal ribs engaged in an equal number of respective longitudinal slots.

Although the invention herein has been described with reference to particular embodiments in which a collapsible mitral valve is deployed into the native mitral annulus of a patient, it is to be understood that the invention contemplates embodiments in which the delivery device 10 is used to deploy other self-expanding medical implants. For example, the delivery device 10 may be used to deploy a collapsible aortic valve into the native aortic annulus of a patient, or to deploy a collapsible stent into a patient.

Although the invention herein has been described with reference to particular embodiments in which the catheter assembly is inserted into the patient through the apex of the heart (i.e., transapical insertion), it is to be understood that the invention contemplates embodiments in which the catheter assembly 16 extends through a portion of the vasculature of the patient to reach the heart, for example, through a transfemoral or subclavian artery. In such embodiments, some of the device components may have to be oriented in a different direction to that described herein. For example, the invention contemplates embodiments in which the distal portion of the catheter assembly 16 approaches the mitral valve from the upstream side as well as from the downstream side of the valve.

It will be appreciated that the various dependent claims and the features set forth therein can be combined in different ways than presented in the initial claims. It will be appreciated that any of the features described in connection with individual embodiments may be shared with others of the described embodiments.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In summary, the disclosure herein recites multiple embodiments to summarize the foregoing. Described herein is a delivery device for a collapsible prosthetic heart valve. The delivery device may include a catheter assembly and an operating handle coupled to the catheter assembly. The catheter assembly may include an inner shaft around which a compartment is defined, and a distal sheath having a proximal segment and a distal segment together configured to enclose the compartment. The operating handle may include a housing defining a movement space therein, the movement space extending in an elongation direction, a first elongated element fixedly coupled to the proximal segment of the distal sheath and moveable in first and second opposite longitudinal directions within the movement space, a second elongated element coupled to the distal segment of the distal sheath and moveable in the first and second longitudinal directions within the movement space, a first actuator coupled to the housing and moveable relative to the housing, the first actuator being operatively engaged with the first elongated element, and a second actuator coupled to the housing and moveable relative to the housing and relative to the first actuator, the second actuator being operatively engaged with the second elongated element. At least a portion of the first and second elongated elements may overlap in the elongation direction. Each of the first and second elongated elements may be independently longitudinally slidable relative to the other of the first and second elongated elements; and/or the operating handle may include an interference member that in a first condition prevents movement of the first elongated element in the first longitudinal direction beyond a limit position, and that in a second condition permits movement of the first elongated element in the first longitudinal direction beyond the limit position; and/or the operating handle may include a releasable lock that in a first condition prevents movement of the second elongated element in the second longitudinal direction, and that in a second condition permits movement of the second elongated element in the second longitudinal direction; and/or the operating handle may include an interference member that in a first condition prevents movement of the first elongated element in the first longitudinal direction beyond a limit position and prevents movement of the second elongated element in the second longitudinal direction, and that in a second condition permits movement of the first elongated element in the first longitudinal direction beyond the limit position and permits movement of the second elongated element in the second longitudinal direction; and/or the inner shaft may be fixedly coupled to the distal segment of the distal sheath and removably coupled to the second elongated element; and/or the first elongated element may be a first lead screw and the second elongated element may be a second lead screw, the first actuator may be a first knob and the second actuator may be a second knob, and the first and second knobs may be threadedly engaged with the first and second lead screws, respectively; and/or the first lead screw may be configured for movement within a central bore of the first knob and within a central bore of the second knob; and/or the housing of the operating handle may include distal and proximal portions that are separated from one another by the first and second knobs; and/or the second lead screw may be rotationally locked to the first lead screw; and/or one of the first and second lead screws may have a rib extending in the first and second longitudinal directions and the other of the first and second lead screws may have a slot extending in the first and second longitudinal directions, the rib being engaged in the slot; and/or the first lead screw may have external threads with a first pitch and the second lead screw may have external threads with a second pitch, the first pitch being different than the second pitch.

Also described herein is an operating handle for a delivery device for a collapsible prosthetic heart valve. The operating handle may include a housing defining a movement space therein, the movement space extending in an elongation direction, a first elongated element moveable in first and second opposite longitudinal directions within the movement space, a second elongated element moveable in the first and second longitudinal directions within the movement space, a first actuator coupled to the housing and moveable relative to the housing, the first actuator being operatively engaged with the first elongated element, and a second actuator coupled to the housing and moveable relative to the housing and relative to the first actuator, the second actuator being operatively engaged with the second elongated element. At least a portion of the first and second elongated elements may overlap in the elongation direction. Each of the first and second elongated elements may be independently longitudinally slidable relative to the other of the first and second elongated elements; and/or the operating handle may include an interference member that in a first condition prevents movement of the first elongated element in the first longitudinal direction beyond a limit position, and that in a second condition permits movement of the first elongated element in the first longitudinal direction beyond the limit position; and/or the operating handle may include a releasable lock that in a first condition prevents movement of the second elongated element in the second longitudinal direction, and that in a second condition permits movement of the second elongated element in the second longitudinal direction; and/or the operating handle may include an interference member that in a first condition prevents movement of the first elongated element in the first longitudinal direction beyond a limit position and prevents movement of the second elongated element in the second longitudinal direction, and that in a second condition permits movement of the first elongated element in the first longitudinal direction beyond the limit position and permits movement of the second elongated element in the second longitudinal direction; and/or the first elongated element may be a first lead screw and the second elongated element may be a second lead screw, the first actuator may be a first knob and the second actuator may be a second knob, and the first and second knobs may be threadedly engaged with the first and second lead screws, respectively; and/or the first lead screw may be configured for movement within a central bore of the first knob and within a central bore of the second knob; and/or the housing of the operating handle may include distal and proximal portions that are separated from one another by the first and second knobs; and/or the second lead screw may be rotationally locked to the first lead screw; and/or one of the first and second lead screws may have a rib extending in the first and second longitudinal directions and the other of the first and second lead screws may have a slot extending in the first and second longitudinal directions, the rib being engaged in the slot; and/or the first lead screw may have external threads with a first pitch and the second lead screw may have external threads with a second pitch, the first pitch being different than the second pitch.

Further described herein is a method of delivering a collapsible prosthetic heart valve in a patient. The method may include providing a delivery device having a catheter assembly and an operating handle. The catheter assembly may include a compartment adapted to receive the valve in an assembled condition and a distal sheath slidable relative to the compartment. The distal sheath may have a proximal segment and a distal segment. The operating handle may include a housing defining a movement space therein and first and second elongated elements each independently moveable in first and second opposite longitudinal directions within the movement space. The method may also include loading the valve into the compartment of the catheter assembly and covering the compartment and the valve with the proximal and distal segments of the distal sheath, and inserting the catheter assembly into the patient so that the valve is positioned at a target location within the patient.

The method may further include partially deploying a first end of the valve by moving the first elongated element in the first longitudinal direction within the movement space, whereby the proximal segment of the distal sheath is moved a first distance in the first longitudinal direction. The method may also include deploying a second end of the valve by moving the second elongated element in the second longitudinal direction within the movement space, whereby the distal segment of the distal sheath is moved in the second longitudinal direction. The method may further include fully deploying the first end of the valve by continuing movement of the first elongated element in the first longitudinal direction within the movement space, whereby the proximal segment of the distal sheath is moved a further distance in the first longitudinal direction; and/or the step of partially deploying the first end of the valve may include moving the first elongated element in the first longitudinal direction from an initial position to a limit position defined by an interference member, and the step of fully deploying the first end of the valve may include moving the interference member to enable the first elongated element to move in the first longitudinal direction beyond the limit position; and/or the step of deploying the second end of the valve may include moving the interference member to enable the second elongated element to move in the second longitudinal direction; and/or the collapsible prosthetic heart valve may be a self-expanding prosthetic mitral valve, the target location may be a native mitral valve annulus, and the step of partially deploying the first end of the valve may release anchor arms of the prosthetic mitral valve adjacent native mitral valve leaflets of the patient; and/or the delivery device may include an inner shaft around which the compartment is defined, the inner shaft being fixedly coupled to the distal segment of the distal sheath and removably coupled to the second elongated element; and/or the method may include, after the step of fully deploying the first end of the valve, uncoupling the inner shaft from the second elongated element and moving the inner shaft relative to the housing to completely cover the compartment with the distal segment of the distal sheath; and/or the steps of partially deploying the first end of the valve and fully deploying the first end of the valve may include rotating a first knob in a single first direction; and/or the step of deploying the second end of the valve may include rotating a second knob in a second direction; and/or the first elongated element may be a first lead screw and the second elongated element may be a second lead screw, and the first and second knobs may be threadedly engaged with the first and second lead screws, respectively; and/or during the step of deploying the second end of the valve, the first lead screw may extend at least partially into a central bore of the first knob and at least partially into a central bore of the second knob; and/or the second lead screw may have an elongated bore configured to receive at least a portion of the first lead screw therein, and the steps of partially deploying the first end of the valve and fully deploying the first end of the valve may each include moving the first lead screw within the elongated bore of the second lead screw.

The invention claimed is:

1. A delivery device for a collapsible prosthetic heart valve, the delivery device comprising:
a catheter assembly including an inner shaft around which a compartment is defined, and a distal sheath having a proximal segment and a distal segment together configured to enclose the compartment; and
an operating handle coupled to the catheter assembly, the operating handle including:
a housing defining a movement space therein, the movement space extending in an elongation direction;
a first elongated element fixedly coupled to the proximal segment of the distal sheath and moveable in first and second opposite longitudinal directions within the movement space;
a second elongated element coupled to the distal segment of the distal sheath and moveable in the first and second longitudinal directions within the movement space, at least a portion of the first and second elongated elements overlapping in the elongation direction, each of the first and second elongated elements being independently longitudinally slidable relative to the other of the first and second elongated elements;
a first actuator coupled to the housing and moveable relative to the housing, the first actuator being operatively engaged with the first elongated element; and
a second actuator coupled to the housing and moveable relative to the housing and relative to the first actuator, the second actuator being operatively engaged with the second elongated element.

2. The delivery device of claim 1, wherein the operating handle includes an interference member that in a first condition prevents movement of the first elongated element in the first longitudinal direction beyond a limit position, and that in a second condition permits movement of the first elongated element in the first longitudinal direction beyond the limit position.

3. The delivery device of claim 1, wherein the operating handle includes a releasable lock that in a first condition prevents movement of the second elongated element in the second longitudinal direction, and that in a second condition permits movement of the second elongated element in the second longitudinal direction.

4. The delivery device of claim 1, wherein the operating handle includes an interference member that in a first condition prevents movement of the first elongated element in the first longitudinal direction beyond a limit position and prevents movement of the second elongated element in the second longitudinal direction, and that in a second condition permits movement of the first elongated element in the first longitudinal direction beyond the limit position and permits movement of the second elongated element in the second longitudinal direction.

5. The delivery device of claim 1, wherein the inner shaft is fixedly coupled to the distal segment of the distal sheath and removably coupled to the second elongated element.

6. The delivery device of claim 1, wherein the first elongated element is a first lead screw and the second elongated element is a second lead screw, the first actuator is a first knob and the second actuator is a second knob, and the first and second knobs are threadedly engaged with the first and second lead screws, respectively.

7. The delivery device of claim 6, wherein the first lead screw is configured for movement within a central bore of the first knob and within a central bore of the second knob.

8. The delivery device of claim 6, wherein the housing of the operating handle includes distal and proximal portions that are separated from one another by the first and second knobs.

9. The delivery device of claim 6, wherein the second lead screw is rotationally locked to the first lead screw.

10. The delivery device of claim 6, wherein one of the first and second lead screws has a rib extending in the first and second longitudinal directions and the other of the first and second lead screws has a slot extending in the first and second longitudinal directions, the rib being engaged in the slot.

11. The delivery device of claim 6, wherein the first lead screw has external threads with a first pitch and the second lead screw has external threads with a second pitch, the first pitch being different than the second pitch.

12. An operating handle for a delivery device for a collapsible prosthetic heart valve, the operating handle comprising:
a housing defining a movement space therein, the movement space extending in an elongation direction;
a first elongated element moveable in first and second opposite longitudinal directions within the movement space;
a second elongated element moveable in the first and second longitudinal directions within the movement space, at least a portion of the first and second elongated elements overlapping in the elongation direction, each of the first and second elongated elements being independently longitudinally slidable relative to the other of the first and second elongated elements;
a first actuator coupled to the housing and moveable relative to the housing, the first actuator being operatively engaged with the first elongated element; and second actuator coupled to the housing and moveable relative to the housing and relative to the first actuator, the second actuator being operatively engaged with the second elongated element.

13. A method of delivering a collapsible prosthetic heart valve in a patient, the method comprising:
providing a delivery device having a catheter assembly and an operating handle, the catheter assembly including a compartment adapted to receive the valve in an assembled condition and a distal sheath slidable relative to the compartment, the distal sheath having a proximal segment and a distal segment, and the operating handle including a housing defining a movement space therein and first and second elongated elements each independently moveable in first and second opposite longitudinal directions within the movement space;
loading the valve into the compartment of the catheter assembly and covering the compartment and the valve with the proximal and distal segments of the distal sheath;
inserting the catheter assembly into the patient so that the valve is positioned at a target location within the patient;
partially deploying a first end of the valve by moving the first elongated element in the first longitudinal direction within the movement space from an initial position to a limit position defined by an interference member, whereby the proximal segment of the distal sheath is moved a first distance in the first longitudinal direction;
deploying a second end of the valve by moving the second elongated element in the second longitudinal direction within the movement space, whereby the distal segment of the distal sheath is moved in the second longitudinal direction; and
fully deploying the first end of the valve by moving the interference member and continuing movement of the first elongated element in the first longitudinal direction beyond the limit position within the movement space, whereby the proximal segment of the distal sheath is moved a further distance in the first longitudinal direction.

14. The method of claim 13, wherein the delivery device further includes an inner shaft around which the compartment is defined, the inner shaft being fixedly coupled to the distal segment of the distal sheath and removably coupled to the second elongated element, the method further comprising, after the step of fully deploying the first end of the valve, uncoupling the inner shaft from the second elongated element and moving the inner shaft relative to the housing to completely cover the compartment with the distal segment of the distal sheath.

15. The method of claim 13, wherein the steps of partially deploying the first end of the valve and fully deploying the first end of the valve include rotating a first knob in a single first direction.

16. The method of claim 15, wherein the step of deploying the second end of the valve includes rotating a second knob in a second direction.

17. The method of claim 16, wherein the first elongated element is a first lead screw and the second elongated element is a second lead screw, and the first and second knobs are threadedly engaged with the first and second lead screws, respectively.

18. The method of claim 17, wherein during the step of deploying the second end of the valve, the first lead screw extends at least partially into a central bore of the first knob and at least partially into a central bore of the second knob.

19. The method of claim 17, wherein the second lead screw has an elongated bore configured to receive at least a portion of the first lead screw therein, and the steps of partially deploying the first end of the valve and fully deploying the first end of the valve each include moving the first lead screw within the elongated bore of the second lead screw.

* * * * *